(12) United States Patent
Shen et al.

(10) Patent No.: US 6,213,998 B1
(45) Date of Patent: Apr. 10, 2001

(54) LASER SURGICAL CUTTING PROBE AND SYSTEM

(75) Inventors: Jin Hui Shen; Karen M. Joos, both of Nashville, TN (US)

(73) Assignee: Vanderbilt University, Nashville, TN (US)

( * ) Notice: Subject to any disclaimer, the term of this patent is extended or adjusted under 35 U.S.C. 154(b) by 0 days.

(21) Appl. No.: 09/054,039

(22) Filed: Apr. 2, 1998

(51) Int. Cl.$^7$ .................................................. A61B 18/18
(52) U.S. Cl. ................................ 606/10; 606/13; 606/16; 606/4; 372/34; 372/70; 372/71
(58) Field of Search ......................... 372/69–72, 34, 372/35.36, 39; 606/2–4, 10, 11, 13, 15–17; 607/88, 89, 93

(56) References Cited

U.S. PATENT DOCUMENTS

| | | |
|---|---|---|
| 4,665,529 | 5/1987 | Baer et al. ............................ 372/107 |
| 4,723,257 | 2/1988 | Baer et al. ............................ 372/108 |
| 4,794,615 * | 12/1988 | Berger et al. . |
| 4,808,789 * | 2/1989 | Muncheryan . |
| 4,846,172 | 7/1989 | Berlin ................................ 128/303.1 |
| 4,852,567 * | 8/1989 | Sinofsky ................................ 606/16 |
| 4,887,592 | 12/1989 | Loertscher ................................ 606/5 |
| 5,066,291 | 11/1991 | Stewart ................................ 606/3 |
| 5,074,861 | 12/1991 | Schneider et al. ...................... 606/17 |
| 5,246,436 | 9/1993 | Rowe ................................ 606/13 |
| 5,263,951 | 11/1993 | Spears et al. ........................... 606/12 |
| 5,304,172 * | 4/1994 | Manoukian et al. .................... 606/15 |
| 5,349,590 | 9/1994 | Amirkhanian et al. .................. 372/6 |
| 5,390,204 | 2/1995 | Yessik et al. ............................ 372/38 |
| 5,407,443 | 4/1995 | Kobayashi et al. ..................... 606/3 |
| 5,423,798 | 6/1995 | Crow ................................ 606/4 |
| 5,568,503 * | 10/1996 | Omori ................................ 606/17 |
| 5,599,341 | 2/1997 | Mathis et al. ............................ 606/5 |
| 5,603,710 | 2/1997 | Easley et al. ........................... 606/15 |
| 5,608,742 | 3/1997 | Peterson ................................ 372/6 |
| 5,675,604 * | 10/1997 | Durkin et al. ........................... 372/75 |
| 5,782,823 * | 7/1998 | Mueller ................................ 606/15 |

OTHER PUBLICATIONS

Georgescu, *Opt. Comm.*, vol. 81:3,4 (Feb. 15, 1991) pp. 186–192.
Dinerman, et al., *Opt. Letters*, vol. 19:15 (Aug. 1, 1994) pp. 1143–1145.
Dinerman, et al., *Adv. Sol. State Laser*, vol. 13 (Feb. 17, 1992) pp. 152–155.
Pollack, et al., *J. Appl. Phys.*, vol. 70;12 (Dec. 15, 1991) pp. 7227–7239.
Dickinson, et al., *J. Modern Optics*, vol. 36:10 (Apr. 14, 1989) pp. 1393–1400.
Esterowitz, *Opt. Engineering*, vol. 29:6 (Jun. 1990) pp. 676–680.
Hamilton, et al., *Opt. Letters*, vol. 19:20 (Oct. 15, 1994) pp. 1627–1629.
Luthy, et al., *Infrared Phys.*, vol. 32: (1991) pp. 283–290.
Merberg, *Lasers in Sur. & Med.*, vol. 13: (Jun. 9, 1993) pp. 572–576.
Brazitikos, et al., "Erbium: YAG Laser Surgery of the Vitreous and Retina", *Ophthalmology*, vol. 102 No.2 (Feb. 1995) pp. 278–290.

(List continued on next page.)

*Primary Examiner*—Linda C. M. Dvorak
*Assistant Examiner*—Bryan K. Yarnell
(74) *Attorney, Agent, or Firm*—Waddey & Patterson; Mark J. Patterson

(57) ABSTRACT

A surgical laser system combines a laser diode array remotely connected to a hand-held surgical probe by a fiber bundle. The surgical system has a which includes a laser head which produces a laser beam for surgical tissue ablation that is delivered through a disposable intraocular probe tip. The probe tip is made of a short section of optical fiber. Preferably, the laser head is an Er:YAG rod pumped by energy from the laser diode array to operate at a wavelength of 2.94 microns. Auxiliary water and thermal electric cooling integral to the hand piece cools the laser head.

13 Claims, 5 Drawing Sheets

OTHER PUBLICATIONS

Shen, et al., "Investigation of a Laser–Phaco Device for Cararact Surgery", Paper presentation Golden Apple Dinner Theater, Abstract No. 3707.

Takasoh, et al., "Intraocular Contact Sclerostomy with Erbium Laser and Intraocular Fiber Type", *Investigative Ophthalmology And Visual Science*,Mar. 15, 1994, vol. 35, No. 4, Abstract No. 3763.

Rivera et al., "Endoscopic Goniotomy with the Erbium: YAG Laser"*Investigative Ophthalmology And Visual Science*, Mar. 15, 1994, vol. 35, No. 4, Abstract No. 3764.

Alimpiev, et al., *Int. Jou. Of Opt.*, vol. 3:4 (1988) pp. 333–344.

* cited by examiner

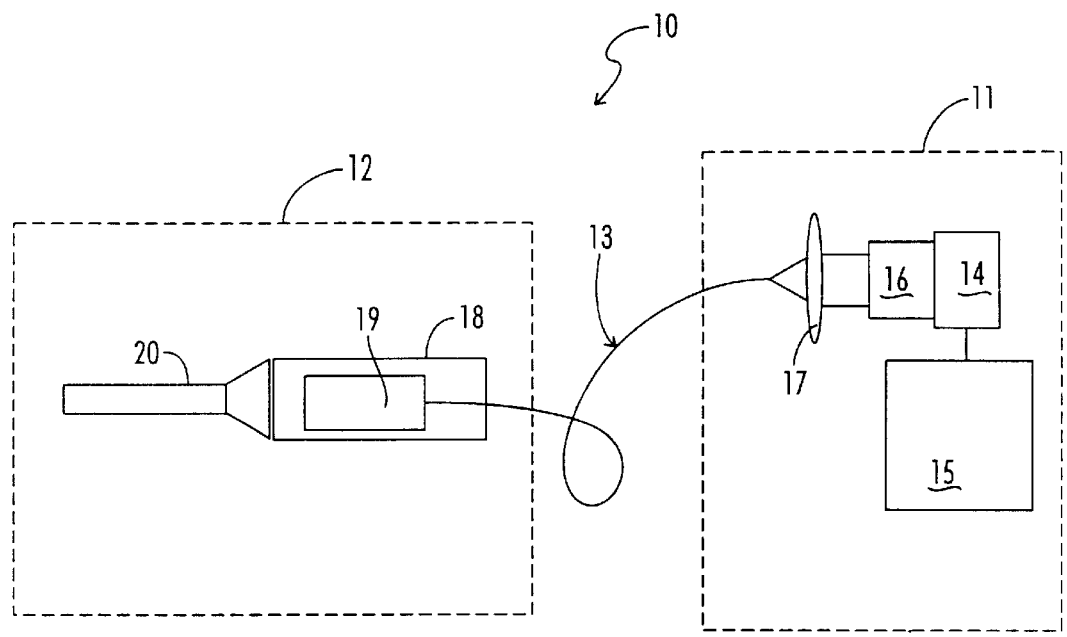
*FIG. 1*
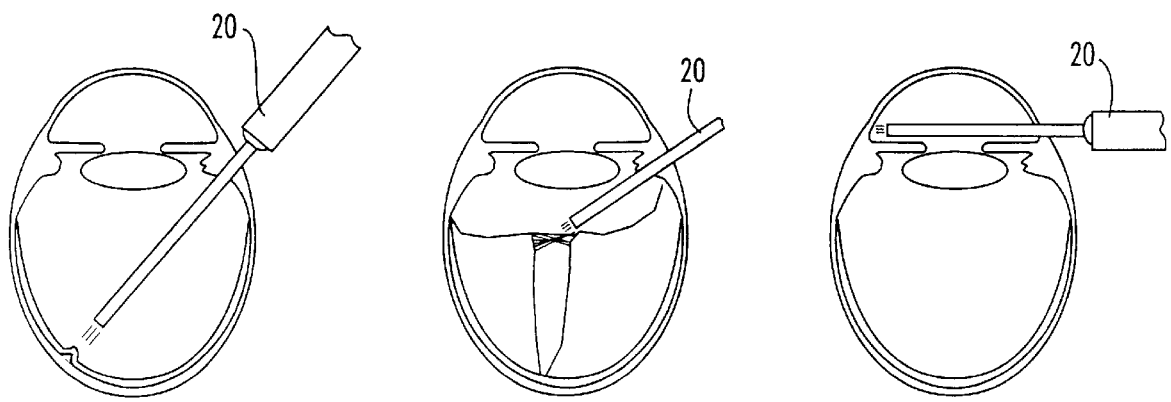
*FIG. 2a*  *FIG. 2b*  *FIG. 2c*

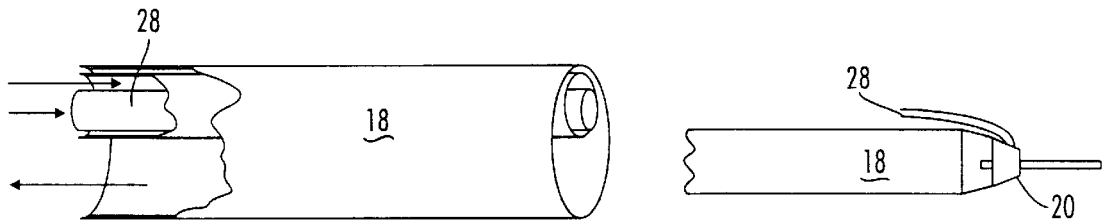
*FIG. 10a*
*FIG. 10b*
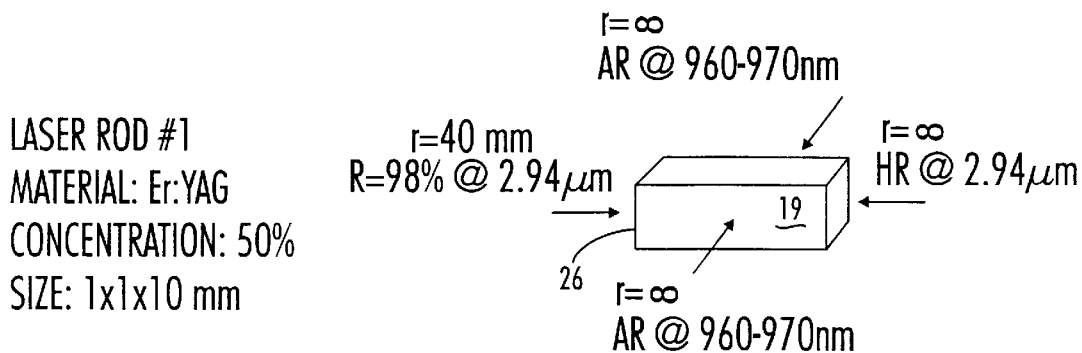
LASER ROD #1
MATERIAL: Er:YAG
CONCENTRATION: 50%
SIZE: 1x1x10 mm
r=radius; R=reflectivity; AR=anti-reflective coating; HR=high-reflective coating
*FIG. 11a*
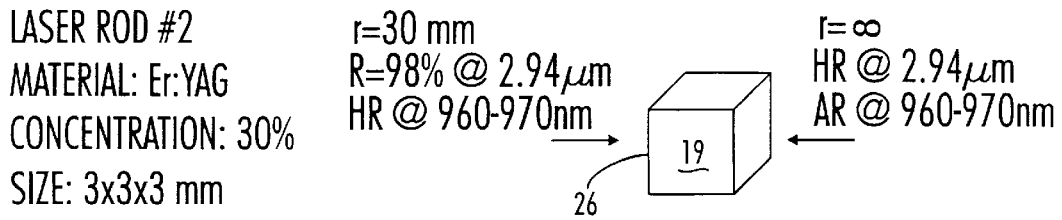
LASER ROD #2
MATERIAL: Er:YAG
CONCENTRATION: 30%
SIZE: 3x3x3 mm
r=radius; R=reflectivity; AR=anti-reflective coating; HR=high-reflective coating
*FIG. 11b*

LASER SURGICAL CUTTING PROBE AND SYSTEM

BACKGROUND OF THE INVENTION

The present invention relates generally to laser cutting probes for use in surgical procedures. More particularly, this invention pertains to a solid-state erbium laser surgical cutting probe and system for use in surgical procedures requiring high precision, including intraocular surgical procedures such as retinotomy, vitrectomy, retinectomy, capsulotomy, sclerostomy, and goniotomy.

Laser cutting, ablation and vaporization are common techniques in surgery. For example, the $CO_2$ laser has been used in dermatology for cutting tumors. Corneal cutting and reshaping is being performed with excimer photorefractive surgery (PRK). The best laser wavelength for many procedures is the wavelength having the highest absorption in tissue. Because water comprises the highest component of the tissue, the best water absorption wavelength often has the best cutting effect.

The most commonly used lasers for cutting are $CO_2$ laser at 10.6 $\mu$m (water absorption coefficient=$8.5\times10^2$/cm$^{-1}$), and Er:YAG at 2.94 $\mu$m, (water absorption coefficient=$1.3\times10^4$/cm$^{-1}$).

Intraocular cutting techniques are needed for ophthalmic surgery. Laser intraocular cutting may improve the surgery with smaller incisions, easier control, and higher precision. Several studies have tried different lasers and various delivery devices to develop this technique.

Lewis A. et al. in the Hebrew University of Jerusalem, Israel, guided an excimer laser beam (193 nm) with an articulated mechanical arm and confined it with a variable-diameter tapered tube (1 mm to 125 $\mu$m in diameter). An air stream was used to push the intraocular liquid out of a cannula and remove fluid from the retina surface just in front of the needle tip. With such an excimer laser delivery system, it was possible to remove retinal tissue accurately without collateral damage.

Dodick J M, et al tried to overcome the delivery problems by conducting a short pulse Nd:YAG laser (1.064 $\mu$m) into the eye with a silica fiber. At the end of the surgical probe, the short pulses hit a titanium target and generated shock waves. This device was applied to fragment nuclear material for cataract extraction.

D'Amico et al delivered Er:YAG laser through a fluoride glass fiber to an endoprobe with sapphire or silica fiber tips ranging from 75 to 375 $\mu$m. This probe was used for transection of vitreous membranes, retinotomy, and incision and ablation of epiretinal membranes. Results showed that twenty-five vitreous membrane transections were made in 16 eyes at distances ranging from 0.5 to 4.5 mm from the retina with radiant exposures ranging from 2 to 50 J/cm2 (0.3–5.5 mJ) with nonhemorrhagic retinal damage in a single transection. Sharp, linear retinotomies were created successfully in five eyes. Epiretinal membrane ablations were performed with radiant exposures ranging from 1.8 to 22.6 J/cm2 (0.3–2 mJ). In aqueous media, results of microscopic examination showed partial- to full -thickness ablation with a maximum lateral thermal damage of 50 $\mu$m. In air- and perfluoro-N-octane-filled eyes, there was increased lateral damage with desiccation of residual tissue. In 12 aqueous-filled eyes, 18 linear incisions were successfully performed, with retinal nonhemorrhagic damage in 2 eyes and hemorrhage in 5. Based on these results, a commercial florid glass delivered Er:YAG laser has been developed for further research (VersaPulse®Select™ Erbium, Coherent®, Palo Alto, Calif.).

Joos K, et al delivered Er:YAG laser (2.94 $\mu$m) through ZrF fiber and coupled to a short piece of sapphire fiber (Saphikon, Inc., Milford, N.H.), or low-OH silica fiber at the end of the intraocular probe. The probe was combined with an endoscope to perform goniotomy in vitro and in vivo. The results showed that minimum tissue damage created with the Er:YAG energy was at an energy level of 2 to 5 mJ per pulse.

Pulsed Er:YAG laser at 2.94 $\mu$m wavelength is capable of cutting human tissue with high precision and little thermal damage to the surrounding tissue. The potential applications include photo-refractive keratectomy, plastic surgery, and intraocular cutting surgery such as retinotomy, vitrectomy, capsulotomy, goniotomy, etc.

To understand the proper use operation of a micro-Er:YAG laser in the surgical applications, it is important to understand its dynamics. The energy level scheme of a 970 nm diode pumped $Er^{3+}$ in a YAG crystal is shown in FIG. 4. The 970 nm diode directly pumps the $Er^{3+}$ to the upper laser energy level. The laser action occurs between the $^4I_{11/2}-^4I_{13/2}$ states. Each of these states is Stark split into about 6 to 7 branch energy levels by the crystal field. These levels are thermally populated as described by a Boltzmann distribution. When the X2 branch of $^4I_{11/2}$ is relatively higher populated than the Y7 branch of $^4I_{13/2}$, the 2.94 $\mu$m laser transition will occur, even when the entire $^4I_{11/2}$ and $^4I_{13/2}$ levels are not inversed. Continuous wave (CW) and quasi-cw laser operations of this transition at room-temperature have been reported with high efficiency and high output power. When the population of $^4I_{13/2}$ accumulates to a certain density, two neighboring $Er^{3+}$ ions can interact. One ion jumps to the higher energy $^4I_{9/2}$ and the other one jumps to the lower level $^4I_{15/2}$. Then the $^4I_{9/2}$ level ion will relax to the upper laser level $^4I_{11/2}$ by rapid multi-photon transition within about 1 $\mu$s. This is called the up-conversion process. It is responsible for shortening the lifetime at the lower laser level which simultaneously leads to excitation of the upper laser level.

Since lifetime at the $^4I_{11/2}$ level is shorter than at the $^4I_{13/2}$ level, highly doped crystals such as YAG:$Er^{3+}$ at 50% concentration have to be used to reduce the lifetime at the lower laser levels, and increase the probability of interaction at the lower level laser ions All commercial Er:YAG lasers presently are flash light pumped. Some of the companies which produce the Er:YAG lasers are: Big Sky, SEO, LSD, Kigre, FOTONA, Quantex, etc. The most common feature of these lasers are: wavelength—2.94 $\mu$m; pulse length—150 to 300 $\mu$s; energy per pulse—100 to 1000 mJ; and repetition rate—1 to 20 Hz.

Other manufacturers (e.g. Coherent, Premier, and Candela) produce fluoride glass delivered Er:YAG laser. Because all fluoride glass fibers can not withstand high laser power, these lasers normally have outputs of less than 20 mJ per pulse of energy.

Kigre Inc. produces a small Er:YAG laser, which places a small flash light pumped Er:YAG laser head into a pistol style hand piece. However, it requires high voltage power for the flash light and the hand piece is not small enough for intraocular surgery.

There is no commercialized diode pumped Er:YAG laser. Theoretical and preliminary experiments showed that a diode pumped Er:YAG laser has a much higher conversion efficiency (10% to 20%) than flash light pumped ones (efficiency <2%). Dinerman, et. al. used a 970 nm diode laser and a Ti:sapphire laser to end pump a 3 mm long Er:YAG laser. This produced 143 mW of cw power when the pump power was 718 mW. Hamilton, et. al. pumped a 2×2×14 mm Er:YAG laser rod with a pulsed diode laser array bar with 200 W peak power, and reached the maximum output energy of 7.1 mJ per pulse at 100 Hz repetition rate. The parameters and results of these experiments are listed in Table I:

TABLE 1

Previous experiments of diode pumped Er:YAG lasers

| | | Er:YAG #1 | Er:YAG #2 | Er:YAG #3 |
|---|---|---|---|---|
| Pump source parameters: | wavelength: | 970 nm | 963 nm | 963 nm |
| | Max. peak power: | 718 mW | 200 W | 200 W |
| | Max. pulse energy: | cw | 88 mJ | 88 mJ |
| | pulse length: | | 400 μs | 400 μs |
| Er:YAG laser parameters: | rod size: | Φ3 × 3 mm | 2 × 2 × 14 mm | 1 × 1 × 14 mm |
| | $Er^{3+}$ concentration: | 33% | 50% | 50% |
| | cavity length: | 3 mm | 40 mm | 25 mm |
| | output coupler: | 99.7% | 98% | 98% |
| Output results: | pump threshold: | 410 mW | | |
| | total efficiency: | | 8% | 5.3% |
| | slope efficiency: | 12% | 13% | |
| | Max. peak power: | 171 mW | 17 W | 11.75 W |
| | Max. pulse energy: | cw | 7.1 mJ | 47 mJ |
| | repetition rate: | | 100 Hz | 275 Hz |

These results indicate that using a diode array pumped micro-Er:YAG laser is very promising for low energy requirements.

One of the biggest difficulties in the practical application of the erbium laser for such surgical applications is that none of the available fibers are ideal for the delivery of the laser. In addition to the bulky mechanical articulated arm, fiber optics available for these wavelengths are: fluoride glass fiber, single-crystal sapphire fiber, chalcogenide glass fiber, polycrystalline fiber, and hollow waveguides. Although they offer some ability to deliver different cutting wavelength, all of them have one or more defects of: brittleness, water solubility, toxicity, sensitive to UV exposure, limited mechanical strength, low temperature damage threshold, and low laser damage threshold. The articulated arms and sapphire fibers are not flexible enough for effective use by the surgeon. Although fluoride glass fibers have better flexibility, they are too brittle and their damage energy thresholds are too low for intraocular use.

What is needed, then, is a cutting probe system that is sufficiently flexible and mechanically strong to reliably deliver the energy from an erbium laser for use in intraocular surgery and in other surgical procedures requiring high precision.

SUMMARY OF THE INVENTION

The shortcomings of the prior art have been addressed in this invention by a novel micro Er:YAG laser (2.94 μm) based intraocular surgical probe system.

To avoid the difficulty of fiber delivery of the erbium laser power, the system includes an erbium laser head which fits into a surgical hand piece. The output of the erbium laser from the hand piece is delivered to the surgical field by a short piece of rigid sapphire or low-OH silica fiber which forms a disposable probe tip. The erbium laser head is pumped by diode laser energy delivered by a silica fiber bundle, instead of a high voltage electric powered flash lamp, so that the hand piece is safe and easy to hold.

The probe uses a plug-in style disposable tip which is made of a short piece of silica or sapphire fiber. This probe is capable of delivering a range of 0.5–10 mJ per pulse of 2.94 μm laser energy at approximately at 1–20 Hz. Accordingly, the probe and system can be used to perform vitreoretinal surgery, including retinotomy, vitrectomy, capsulotomy, goniotomy, as well as other superficial surgery where precise tissue cutting is necessary. With an enlarged erbium laser head, the cutting probe of this invention can produce enough energy to perform laser cataract removal.

The laser cutting probe and system of this invention solves the difficulty of delivering Er:YAG laser energy at 2.94 μm. It renders intraocular cutting clinically possible with a laser and may be useful also in other subspecialties which need low energy levels and precise tissue cutting.

BRIEF DESCRIPTION OF THE DRAWINGS

FIG. 1 is a block diagram of a preferred embodiment of the erbium laser surgical system of this invention.

FIGS. 2a, 2b, and 2c are cutaway side views showing positioning of the probe of the system of FIG. 1 during a) retinotomy; b) cutting of vitreous bands; and c) goniotomy.

FIG. 10 is an enlarged side view of another embodiment of the disposable tip of FIGS. 1 and 9, showing an infusion/suction line.

FIGS. 11a and 11b are perspective views of two configurations of Er:YAG laser rods used in the system of FIG. 1.

DESCRIPTION OF THE PREFERRED EMBODIMENTS

Figure 3:
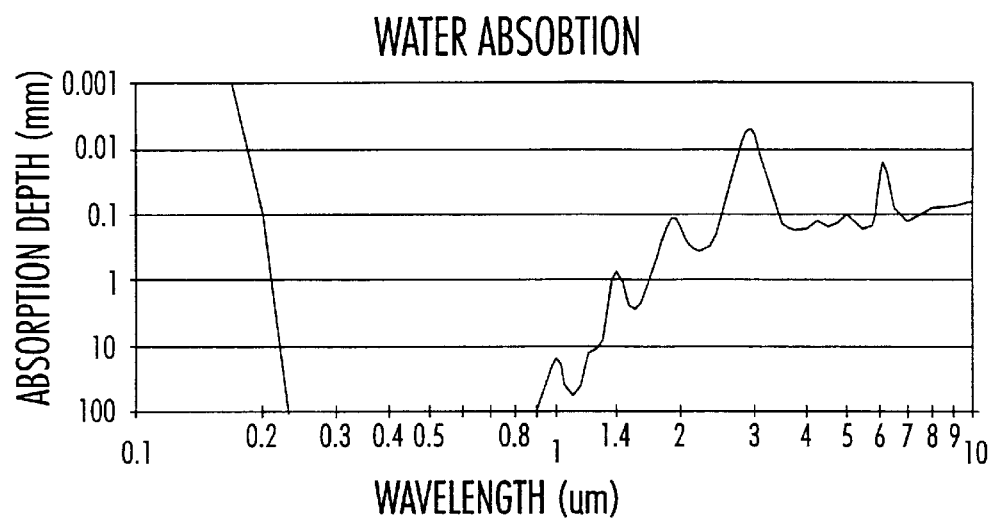
FIG. 3 is a graphical representation showing the level of energy absorption in water as a function of laser wavelength.
Figure 4:
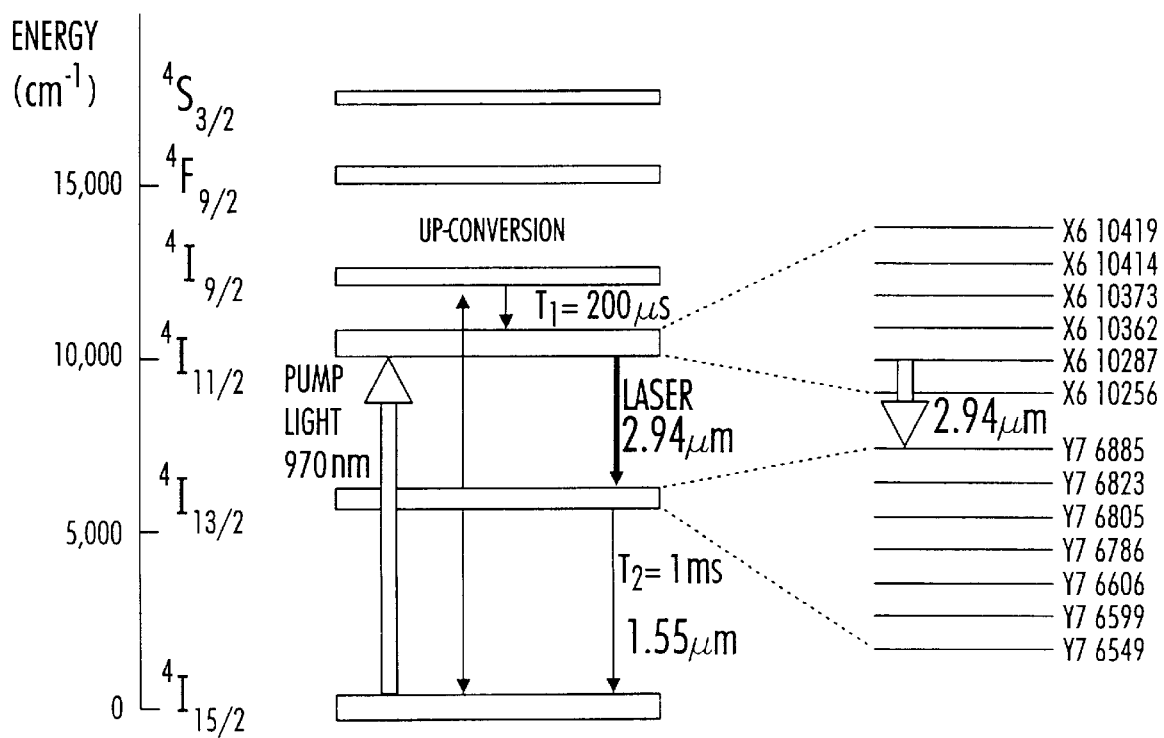
FIG. 4 is a graphical representation of the energy level of a 970 nm diode pumped Er in a YAG crystal.

The novel laser surgical laser cutting system 10 of the present invention is shown in FIG. 1, in which a laser energy source 11 is coupled to a surgical probe assembly 12 by a remote connect assembly 13. The laser energy source 11 preferably combines a diode laser array 14 with a matching power supply 15. The output of the laser diode array 14 passes first through a column lens 16 and then through a focusing lens 17 which directs the laser energy into the input end of a fiber bundle 25 (FIG. 8) as part of remote connect assembly 13.

The novel surgical probe assembly 12 has a hand piece 18 which holds an internal laser head 19. Preferably, the laser head 19 uses a solid-state laser medium such as an erbium-doped yttrium aluminum garnet rod or crystal (Er:YAG). The laser head 19 is connected to the output end of fiber bundle 25. Accordingly, the Er:YAG laser head 19, when pumped by the diode laser energy from the laser energy source 11, will generate and deliver laser radiation at a wavelength of 2.94 microns to and through a disposable probe tip 20.

Figure 9:
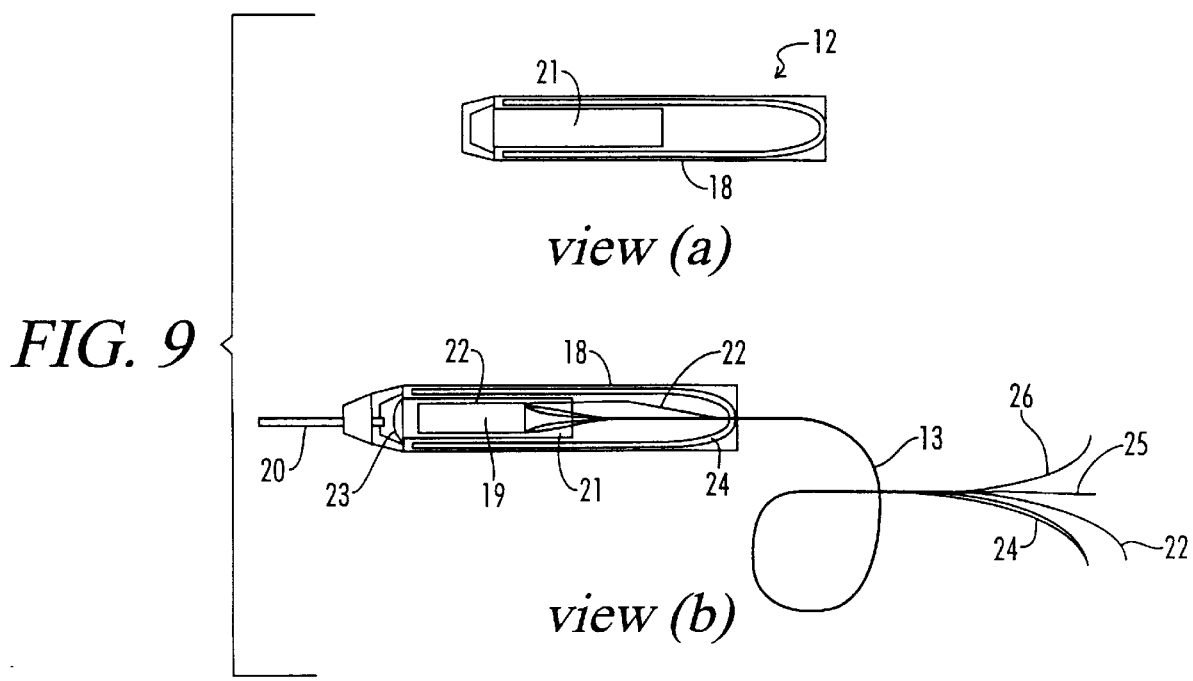
FIG. 9 is an enlarged cutaway side view of the surgical hand piece of the system of FIG. 1.

FIG. 9 provides additional detail about the novel design of the probe assembly 12. The surgical hand piece 18 is sized and shaped to fit easily into the hand of the surgeon. For example, a hand piece 18 having an outside diameter of approximately 15 mm, and length of about 10 to 15 cm, should accommodate the needs of most users. To provide strength, durability, heat dispersion, and ease of sterilization, the hand piece 18 is preferably made of stainless steel or a titanium alloy.

As best seen in view (a) of FIG. 9, the hand piece 18 includes a sealed chamber 21 which supports the micro Er:YAG laser head 19 (FIG. 9(b)) and isolates it from moisture and dust.

Figure 5:
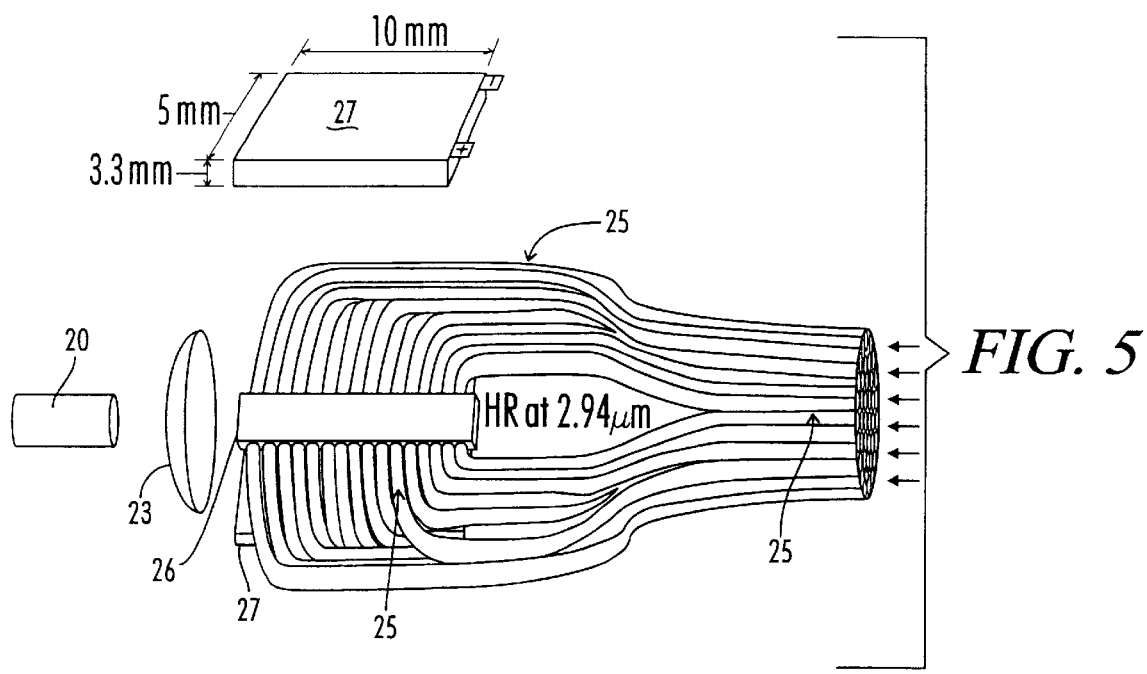
FIG. 5 is a side view of a first embodiment of the laser head used in the system of FIG. 1, in which a side pump configuration is used.
Figure 6:
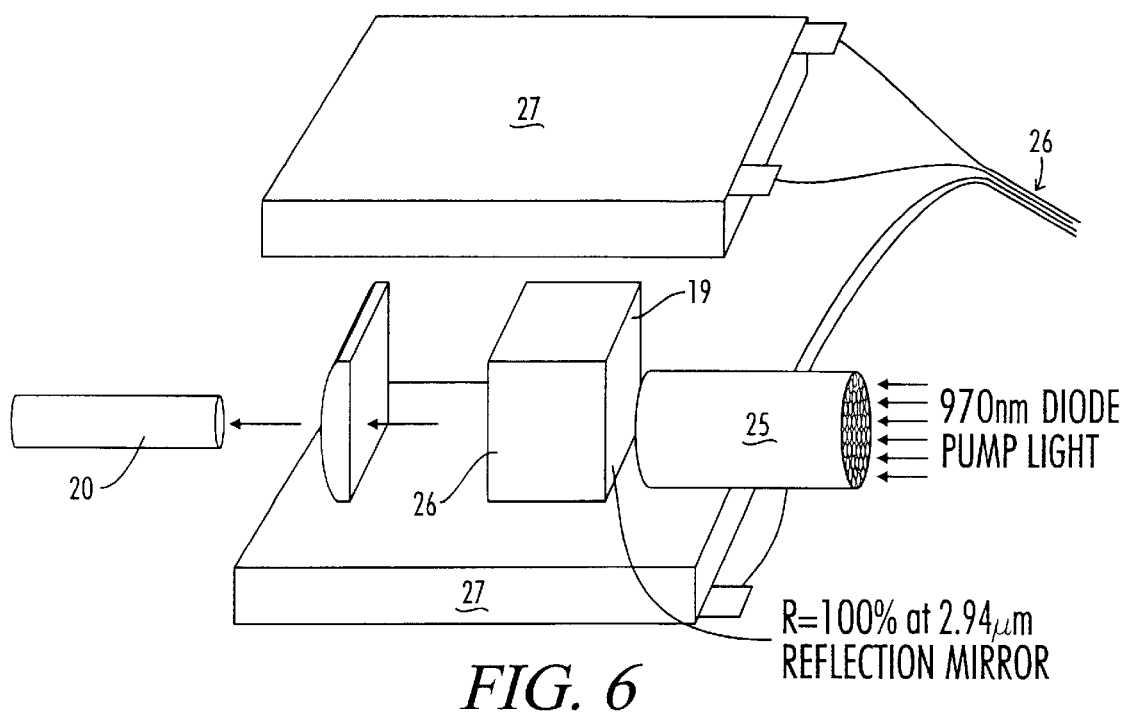
FIG. 6 is a is a side view of a second embodiment of the laser head used in the system of FIG. 1, in which an end pump configuration is used

So that the probe assembly 12 can be effectively used in delicate intraocular surgery, a visible aiming beam should be combined with the 2.94 $\mu$m cutting laser in the probe tip 20. Accordingly, a visible aiming beam is generated externally and delivered to the hand piece 18 via a multi-mode optical fiber 22 as part of remote connect assembly 13. The optical fiber 22 enters the hand piece 18 and is positioned adjacent to the Er:YAG head 19 to deliver the aiming beam through the probe tip 20. As best seen in FIGS. 5 and 6, a sapphire or $CaF_2$ hemisphere ball lens 23 is aligned transversely across the output end of the hand piece 18 and laser head 19. The lens 23 seals the chamber 21 and focuses the output of the laser head 19 into the probe tip 20. The lens 23 is preferably coated with anti-reflection film at 2.94 $\mu$m and will also focus some of the visible light from the aiming beam fiber 22 into the probe tip fiber 20. Therefore, the aiming beam output will be parallel to the 2.94 $\mu$m laser Er:YAG output, making it useful to the surgeon in manipulation of the hand piece 18. Because the Er:YAG laser head 19 itself forms the laser cavity, no special optical alignment is needed. A HeNe laser (not shown) coupled to a 200 $\mu$m diameter fiber 22 can be used to generate the aiming beam.

The Er:YAG laser head 19 generates heat that should be dissipated to avoid overheating of the hand piece 18. To address this need, cooling water is delivered to and circulated around the interior of hand piece 18 by a cooling channel 24, to remove the thermal load from the laser head 19. External to the hand piece 18, the cooling channel 24 is formed of two thin silicone tubes integrated into the remote connect assembly 13, one to deliver the water and one to return the water to a miniature water pump (not shown). To provide temperature monitoring for safety purposes, a temperature sensor, such as a thermocouple (not shown), can be positioned inside the hand piece 18. The output of the temperature sensor is sent to an external temperature monitor (not shown) through electrical wire cable 26, which can be part of the remote connect assembly 13. Preferably, the temperature monitor will have an overheat setpoint that will generate a shut down signal to the laser energy source 11 if an overheat condition occurs.

The overall size of the chamber 21 and laser head 19 should be in the range of 10 mm in diameter, and less than 50 mm in length, so that it will fit into the hand piece 18. FIGS. 5 and 6 show two different configurations for the components internal to the hand piece 18. FIG. 5 illustrates a side pump arrangement in which the individual fibers in the pump light fiber bundle 25 (forming part of connect assembly 13) enter and deliver the pumped laser energy from the laser diode array 14 (FIG. 1) into the sides of laser head 19. In the side pump configuration, the preferred dimensions of the Er:YAG laser rod which forms laser head 19 will be 1×1×10 mm. The $Er^{3+}$ concentration will be 50%. At this doping level, and using a 970 nm diode laser pump light, the transmission depth in the crystal is ~1 mm. As seen in FIG. 11(a), the ends of the Er:YAG rod will be coated with (2.94 $\mu$m wavelength) 100% high reflective and 98% reflective mirror respectively. The high reflective (HR) end of the rod 19 will have a radius of 30 mm and the 98% reflective output coupler 26 will be flat so the Er:YAG rod 19 itself will form a stable oscillator cavity. The two sides which contact the pump fibers 25 will be coated with anti-reflective material at 970 nm wavelength.

In the configuration of FIG. 6, the pumped laser energy is delivered to the end of the Er:YAG laser head 19. As shown in FIG. 11(b), the Er:YAG laser rod 19 is preferably 3×3×3 mm for the end pump configuration, with an $Er^{3+}$ concentration of 30% for a deeper transmission of pump light. The laser oscillator cavity also will be formed by the two ends of the crystal rod. The end of the head 19 which contacts the pump light fiber bundle 25 will be HR at 2.94 $\mu$m, anti-reflective (AR) at 970 nm, and flat. The output coupler 26 will have 99% reflectivity at 2.94 $\mu$m, HR at 970 nm, and have a radius of 30 mm.

The Er:YAG rods 19 as shown in FIGS. 5, 6, and 11 can be obtained from Scientific Materials Corp., Bozeman, Mont.

Figure 7:
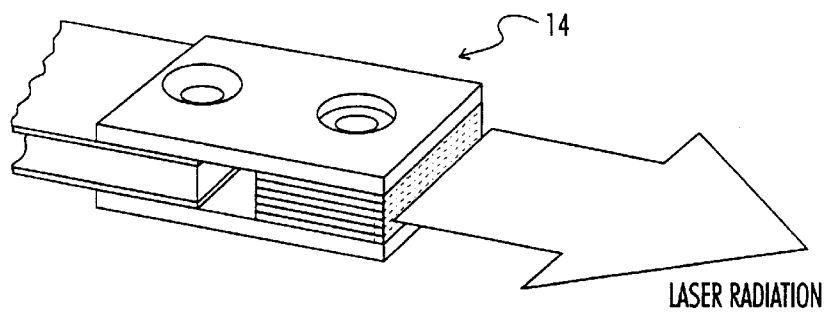
FIG. 7 is an enlarged oblique view of the diode laser array used in the system of FIG. 1.

Instead of using a high voltage powered flash lamp as a pump source, the laser head 19 of the system 10 is pumped by a fiber bundle delivered InGaAs diode laser array at 970 nm wavelength. FIG. 7 is an enlarged view of a typical SDL InGaAs diode laser array 14. The diode laser array model SDL-6231-A6 from SDL, Inc.(970 nm central wavelength) is an idea pump source 14. The SDL InGaAs diode laser array 14 is made up of six one dimensional diode bars, which have an illumination area of 10 mm×1 $\mu$m. The bars are bonded to separate microchannel cooling packages, which, on being stacked to form the array, result in a diode bar spacing of 400 $\mu$m.

The diode array 14 as shown can produce a 400 $\mu$s pulse with up to 360 W peak power at a repetition rate of up to 50 Hz. Considering a pump rate at which 70% of total pump energy is delivered to the Er:YAG rod 19, the Er:YAG laser head 19 can generate 10 mJ per pulse of energy. At 20 Hz repetition rate, the average output power of the diode laser array 14 is 2.88 W. To remove this amount of thermal load in the Er:YAG head 19, auxiliary thermal electric heating panels 27 are positioned inside hand piece 18 immediately above and below the laser head 19. The panels 27, which are conventional in design and operation, are connected to an external low voltage supply through electric cable 26. Coating the thermal electric cooling plates 27 with metal may be necessary for better thermal conduction. The thermal exchange rate of the thermal electric cooling plates 27 (FIGS. 5 and 6) should exceed the average output power of array 14. Such a device is commercially available. The model CP 1.4-3-045L from Melcor Corp. (Trenton, N.J.) has a maximum heat absorption rate of 1.6 W per piece, with a size of 5×10×3.3 mm. The Er:YAG rod 19 is sandwiched between two of these thermal electric cooling plates 27 which can provide up to 3.2 W maximum thermal absorption rate.

Figure 8:
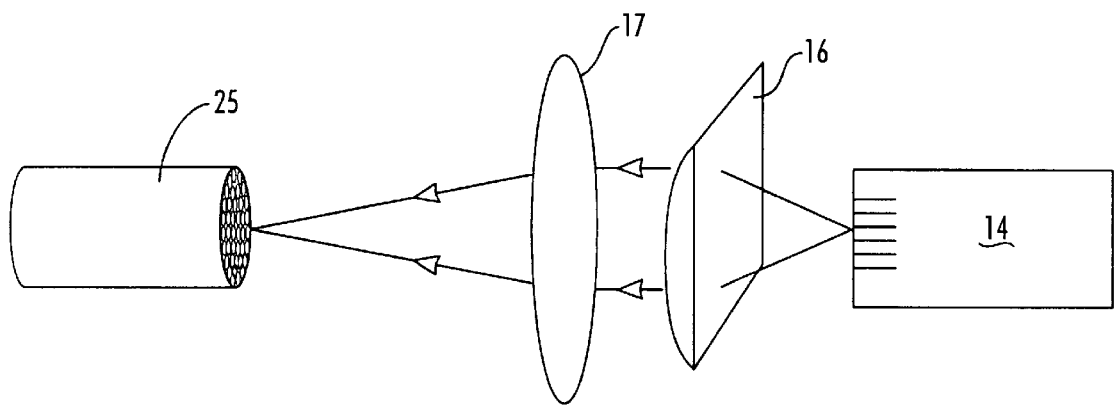
FIG. 8 is an enlarged side view showing the coupling of the output from diode laser array of FIG. 7 into the silica fiber bundle of FIG. 1.

FIG. 8 schematically shows the coupling of the diode laser array 14 into silica fiber bundle 25. Two lenses are be used to couple the diode laser output into the fiber bundle 25. The first is a cylindrical column lens 16, which captures the fast axis of the diode laser array bar and reduces the full-angle divergence close to the slow axis. The second lens 17 focuses the diode laser beam onto the surface of the fiber bundle 25. Since the fiber bundle 25 has a total diameter of approximately 3 mm, such coupling is feasible. In order to increase the coupling efficiency, all of the optical surfaces including the fiber bundle surface will be coated with anti-reflection film. A standard SMA 905 connector can then be used to link the fiber bundle 25 to the 970 nm diode laser source 14. The peak power of the pump light from the laser energy source 11 should be greater than 200 W at a repetition rate of 1–20 Hz.

The fiber bundle 25 can be fabricated from multiple 100 μm or 60 μm core diameter multimode silica fibers bundled for the pump light delivery. Silica fiber is very strong and flexible and is satisfactory for medical applications. The total diameter of the fiber bundle 25 is approximately 3 mm. For the end pump configuration of FIG. 6, the fiber bundle 25 will nearly contact the HR end of the Er:YAG rod 19 (FIG. 11(b)).

For the side pump configuration of FIG. 5, the fibers of bundle 25 are bent 90 degrees under high temperature, and then the fibers are packed to a linear array. Both sides of the Er:YAG rod 19 are in contact with the fiber array. The other ends of these two fiber arrays will be bundled together, and connected to the diode laser pump source 11. The output of the laser head 19 should be 0–10 mJ at 1–20 Hz.

Accordingly, remote connect assembly 13 will preferably integrate (1) the pump light fiber bundle 25 from the diode laser array 14; (2) the electrical cable 26 containing four thin electric wires of 0.36 voltage to power the thermal electric cooling plates 27 and to connect the temperature sensor to the temperature detector, (3) the cooling channel 24; and (4) the single multi-mode fiber 22 for the visible aiming beam.

The probe tip 20 of probe assembly 12 is a plug-in disposable tip which is made of a short piece of silica or sapphire fiber having a diameter of 200 microns. This probe tip 20 is capable of delivering a range of 0.5–10 mJ per pulse of 2.94 μm laser energy at approximately at 1–20 Hz.

As seen in FIG. 10, the disposable tip 20 can incorporate an infusion/suction line 28 to aid in surgery. The infusion/suction line 28 can be attached along the side of the hand piece 18 as shown in FIG. 10(b) or passed through the inside of the hand piece 18. A conventional phacoemulsification machine (not shown) can then be used by the surgical team to control irrigation/aspiration in the surgical field adjacent to the probe tip 20. For example, FIGS. 2a, b, and c show intraocular positioning of the probe tip 20 during retinotomy, cutting of vitreous bands, and goniotomy respectively.

Although a preferred embodiment of the system has been described for use in intraocular surgery, the probe and system of this invention can be adapted to a variety of different surgical procedures where a high degree if precision is required.

Thus, although there have been described particular embodiments of the present invention of a new and useful Laser Surgical Cutting Probe and System, it is not intended that such references be construed as limitations upon the scope of this invention except as set forth in the following claims.

What is claimed is:

1. A system for performing laser surgery comprising:

a. a laser energy source remotely connected to a surgical probe assembly by a remote connect assembly, the remote connect assembly including a fiber bundle adapted to transmit laser pump energy from the laser energy source;

b. the surgical probe assembly comprising a hand piece having a size and shape adapted for gripping, a chamber internal to the hand piece, the chamber enclosing a laser head, and a probe tip, the chamber being sealed against entry of moisture and dust; and c. the laser head operatively coupled to the fiber bundle to receive the laser pump energy whereby the laser pump energy causes the laser head to generate a beam of laser radiation at a predetermined wavelength and energy level, the beam of laser radiation optically coupled to and directed through the probe tip, the fiber bundle having an output end that is closely proximate to or in contact with an external coupling surface portion of the laser head, the output end of the fiber bundle covering substantially all of the coupling surface portion of the laser head.

2. The system of claim 1 wherein the probe tip comprises a piece of optical fiber removably attached to the hand piece whereby the probe tip can be separated from the hand piece and laser head to be disposed of and replaced after use.

3. The system of claim 1 further comprising a suction/infusion line adapted for delivering and removing fluids proximate the probe tip.

4. The system of claim 1 wherein the fiber bundle comprises a plurality of bundled silica fibers.

5. The system of claim 1 whereby the laser energy source comprises a diode laser array generating the laser pump energy at a wavelength of 970 nm and the laser head comprises an Er:YAG rod whereby the beam of laser radiation has a wavelength of 2.94 microns.

6. The system of claim 5, the laser energy source further comprising a column lens and a focusing lens aligned in an optical path between the laser diode array and the fiber bundle.

7. The system of claim 5 wherein the fiber bundle is side coupled to the Er:YAG rod.

8. The system of claim 5 wherein the fiber bundle is end coupled to the Er:YAG rod.

9. The system of claim 5, the surgical probe assembly further comprising means to deliver a visible guide beam indicating the position of the beam of laser radiation.

10. The system of claim 1 wherein the surgical probe assembly further comprises auxiliary cooling means integral to the hand piece.

11. The system of claim 10, the auxiliary cooling means comprising a thermal electric cooler proximate the laser head.

12. The system of claim 10, the auxiliary cooling means comprising a recirculating fluid channel.

13. The system of claim 1 wherein the laser head comprises a crystal rod having flat end portions forming an oscillator cavity.

* * * * *